(12) United States Patent
Lee

(10) Patent No.: US 7,410,534 B2
(45) Date of Patent: Aug. 12, 2008

(54) AIR PURIFIER FOR INDUSTRIAL PLANTS

(75) Inventor: Hui-Hsiung Lee, Taipei (TW)

(73) Assignee: Race Ahead Technology Limited, Tortola (VG)

( * ) Notice: Subject to any disclaimer, the term of this patent is extended or adjusted under 35 U.S.C. 154(b) by 10 days.

(21) Appl. No.: 11/470,097

(22) Filed: Sep. 5, 2006

(65) Prior Publication Data
US 2008/0053311 A1 Mar. 6, 2008

(51) Int. Cl.
*B01D 47/00* (2006.01)
(52) U.S. Cl. .................. 96/224; 422/24; 422/186.3
(58) Field of Classification Search .............. 96/224, 96/270, 271, 273, 322; 422/24, 186.3
See application file for complete search history.

(56) References Cited
U.S. PATENT DOCUMENTS 5,256,379 A * 10/1993 DeLoach ............... 422/186.3
5,833,740 A * 11/1998 Brais ........................ 96/16
5,861,123 A * 1/1999 Schifftner ................ 422/24
5,935,525 A * 8/1999 Lincoln et al. ........... 422/121
6,022,511 A * 2/2000 Matschke ................ 422/121
6,315,963 B1 * 11/2001 Speer .................... 422/186.3
7,108,837 B2 * 9/2006 Kato et al. .............. 422/186.3

* cited by examiner

*Primary Examiner*—Duane Smith
*Assistant Examiner*—Sonji Turner

(57) ABSTRACT

An air purifier for industrial plants has an ultraviolet (UV) cleaner. The UV cleaner has a duct casing, multiple UV generators and an air pump. The duct casing has a cavity defined in the duct casing, an air inlet communicating with the cavity and an air outlet communicating with the cavity. The UV generators are mounted in the cavity in the duct casing and generate UV when in operation. The air pump is connected to the air outlet and generates an outward air suction force through the air outlet. The air purifier operates without any filtering elements and has an excellent filtering rate.

3 Claims, 3 Drawing Sheets

AIR PURIFIER FOR INDUSTRIAL PLANTS

BACKGROUND OF THE INVENTION

1. Field of the Invention

The present invention relates to a purifying device, and more particularly to an air purifier for industrial plants and that purifies dirty air.

2. Description of Related Art

Industrial plants such as oil refineries and incinerators generate a large quantity of dirty air, which will pollute the ambient environment and endanger human health.

To clean the dirty air before it discharges out from the plants and becomes a significant hazard to ambient environment and people, the plants are equipped with an air purifier that purifies the dirty air.

Conventional air purifiers are classified into two types. One type is air filters and the other type is air cleaning agents.

A conventional air filter may be a filter net or an active carbon filter element having multiple meshes. When the air passes through the meshes, the air filter captures the pollutants in the air. However, dimensions of the meshes are too small and therefore the filtering rate of the air filter is low.

A conventional air cleaning agent is emitted to mix with the dirty air and react with the pollutants in the air. The product from the reaction of the air cleaning agent and the pollutants is harmless to people and ambient environment. However, the rest of the air cleaning agent due to the incomplete reaction would be harmful to people. Furthermore, the product from the reaction may smell and un-comfort people.

To overcome the shortcomings, the present invention provides an air purifier to mitigate or obviate the aforementioned problems.

SUMMARY OF THE INVENTION

The main objective of the invention is to provide an air purifier that purifies dirty air.

An air purifier for industrial plants in accordance with the present invention comprises an ultraviolet (UV) cleaner. The UV cleaner has a duct casing, multiple UV generators and an air pump. The duct casing has a cavity defined in the duct casing, an air inlet communicating with the cavity and an air outlet communicating with the cavity. The UV generators are mounted in the cavity in the duct casing and generate UV when in operation. The air pump is connected to the air outlet and generates an outward air suction force through the air outlet.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
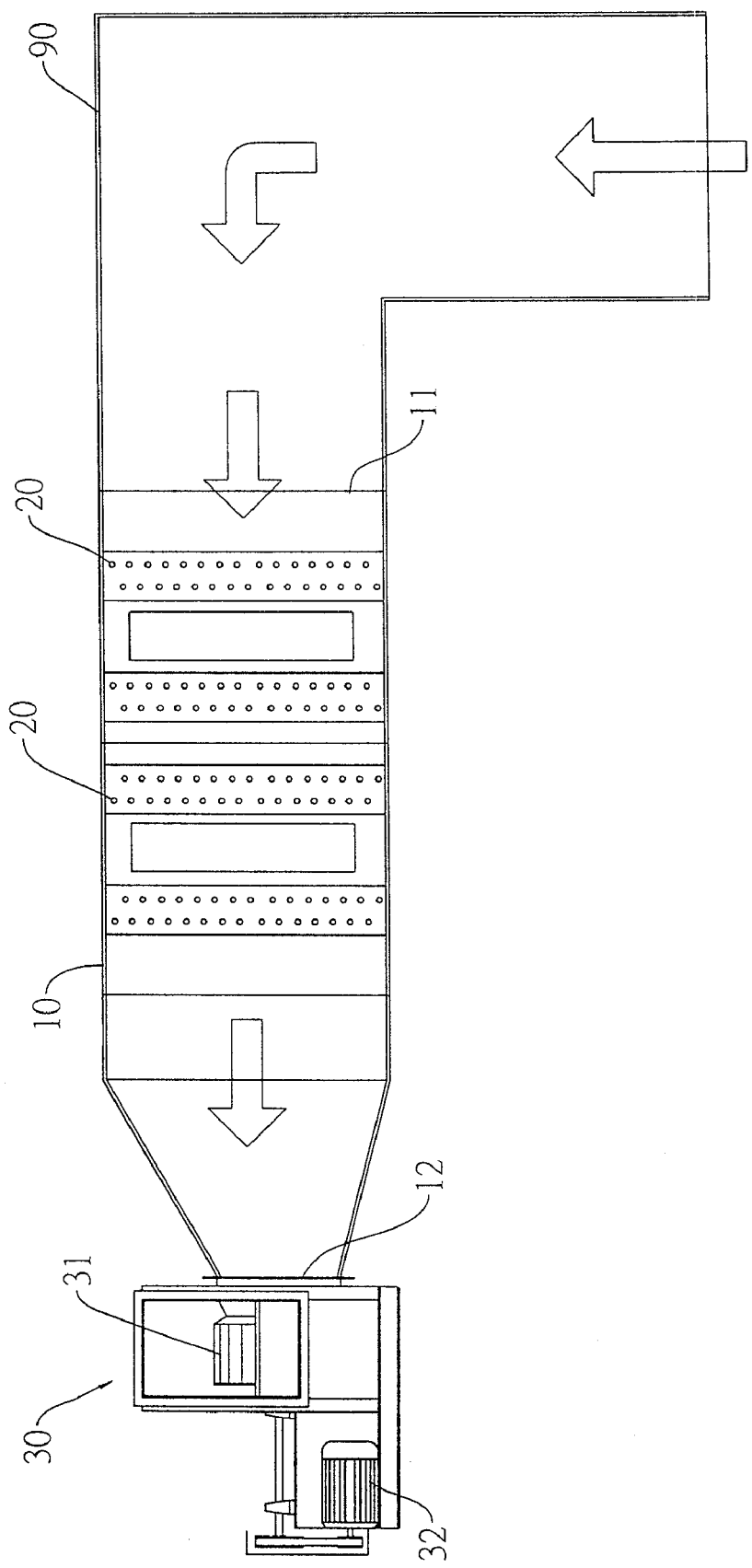
FIG. 1 is a side view in partial section of an air purifier for industry plants in accordance with the present invention connected to the air duct, wherein the arrows illustrates the airflow.
Figure 2:
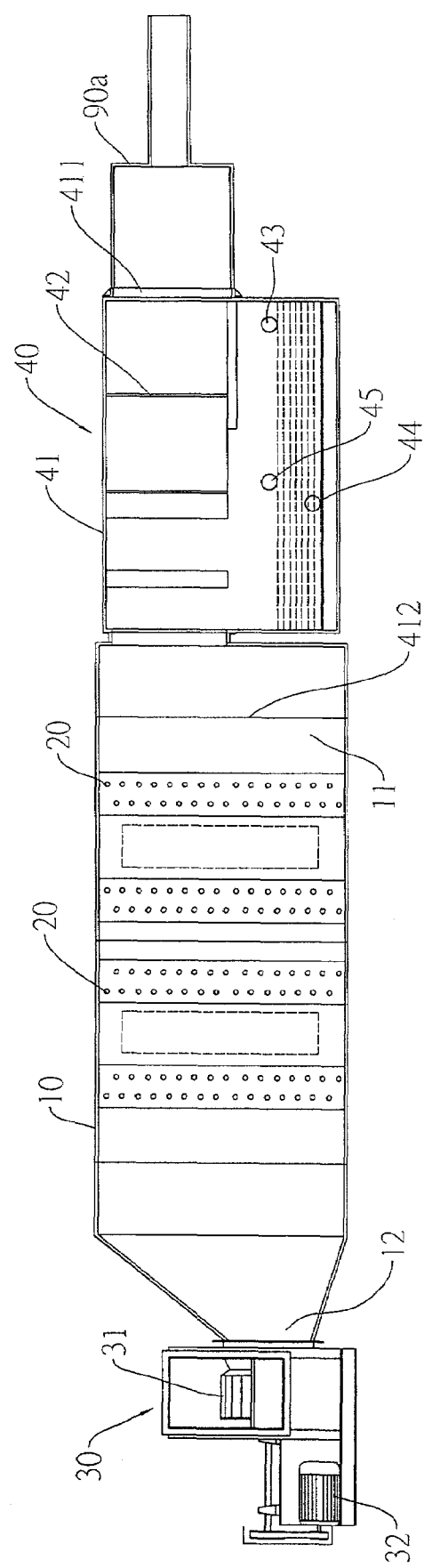
FIG. 2 is a side view in partial section of the air purifier in FIG. 1 with the water cleaner connected to the air duct, wherein the arrows illustrate the airflow.
Figure 3:
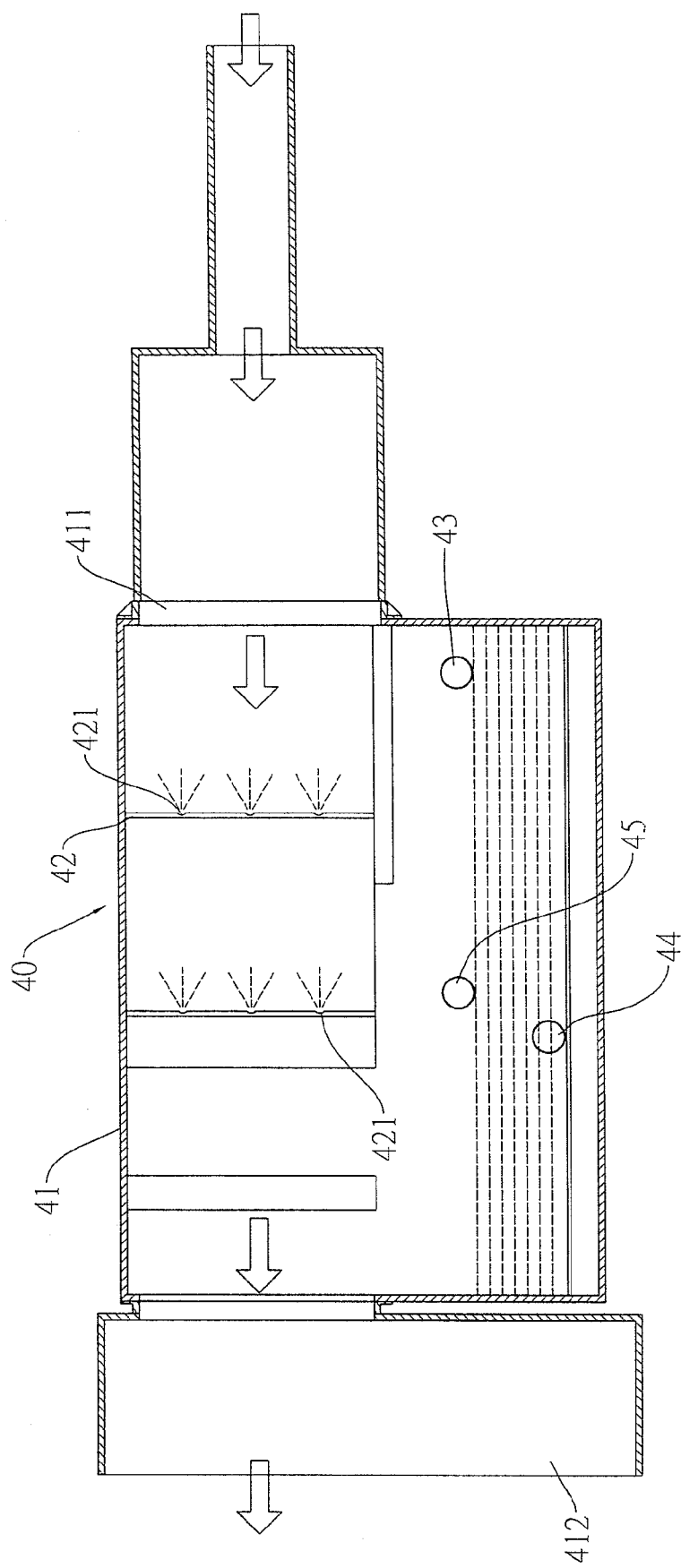
FIG. 3 is an enlarged side view in partial section of the water cleaner of the air purifier in FIG. 2.

With reference to FIGS. 1-3, an air purifier in accordance with the present invention is used with an air duct (90, 90*a*) connected to air outlet of an industrial plant such as an oil refinery or an incinerator.

The air purifier comprises an ultraviolet (UV) cleaner and a water cleaner (40).

The UV cleaner may be connected to the air duct (90) to clean and purify dirty air from the operating industrial plant and has a duct casing (10), multiple UV generators and an air pump (30).

The duct casing (10) is hollow and may be connected to the air duct (90), and the duct casing (10) has a cavity, an air inlet (11) and an air outlet (12). The cavity is defined in the duct casing (10). The air inlet and outlet (11, 12) communicate with the cavity, and the air inlet (11) may be connected to the air duct (90).

The UV generators (20) may be UV light tubes and are mounted in the duct casing (10). The UV generators (20) generate two types of UV when in operation. One type of the UV has a wavelength in an extent from 160 to 200 nanometer (nm), and the other type of the UV has a wavelength in an extent from 220 to 300 nm. The two types of the UV decompose most kinds of pollutants such as volatile organic compounds (VOCs), nitroxides (NOx) and sulfoxides (SOx) and eliminate bacteria in the dirty air from the industrial plant. The pollutants in the air irradiated by the UV generators (20) turn into non-poisonous, flavorless material that would not endanger ambient environment and not harm people.

The air pump (30) is connected to the air outlet (12) of the duct casing (10) and generates an outward air suction force through the air outlet (12) when operating. The air pump (30) may have a fan (31) mounted outside the air outlet (12) in the duct casing (10) of the UV cleaner and a motor (32) connected to and drives the fan (31) through a transmission device. When an air flow due to the air suction force passes through the duct casing (10), the UV radiated from the UV generators (20) decompose the pollutants and bacteria in the air flow and purifying the air flow. The purified air is discharged out from the air outlet (12).

The water cleaner (40) may be connected to the UV cleaner and the air duct (90*a*) and has a duct casing (41), multiple sprinkling tubes (42), an inlet hose (43), an outlet hose (44) and an overflow hose (45).

The duct casing (41) of the water cleaner (40) is connected to the duct casing (10) of the UV cleaner and the air duct (90*a*) and has a cavity, an air inlet (411) and an air outlet (412). The cavity is defined in the duct casing (41) of the water cleaner (40). The air inlet (411) and outlet (412) communicate with the cavity in the duct casing (41) of the water cleaner (40).

The sprinkling tubes (42) are mounted in the cavity in the dust casing (41) of the water cleaner (40) and may be connected to an external water source to sprinkle water. Each sprinkling tube (42) has multiple nozzles (421). The nozzles (421) are defined in the sprinkling tube (42), face the air inlet (411) in the duct casing (41) of the water cleaner (40) and may sprinkle water to absorb pollutant particles in the air.

The inlet hose (43) is mounted in the duct casing (41) of the water cleaner (40), communicates with the cavity of the duct casing (41) and may be coilliected to an external water source to pour water into the cavity in the duct casing (41).

The outlet hose (44) is mounted in the duct casing (41) of the water cleaner (40), communicates with the cavity of the duct casing (41) and may discharge water out of the cavity in the dust casing (41). After the sprinkled water absorbs the pollutant particles in the water and falls down to mix with the clean water from the inlet hose (43), the outlet hose (44) discharges the contaminated water mixed with the pollutant particle out from the duct casing (41).

The overflow hose (45) is mounted in the duct casing (41) of the water cleaner (40) above the outlet hose (44) and communicates with the cavity of the duct casing (41) and may discharge the overflowing water out of the cavity.

The air purifier with the water cleaner (40) sprinkling water to absorb pollutants in the air and the UV cleaner decomposing the rest of the pollutants operates without any filtering elements and has a low filtering rate to purify the air quickly. Furthermore, the air purifier without any air cleaning agents neither smells and discomforts people nor leaves remaining air cleaning agents in the air to endanger people and ambient environment.

Even though numerous characteristics and advantages of the present invention have been set forth in the foregoing description, together with details of the structure and function of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An air purifier for industrial plants comprising
    an ultraviolet (UV) cleaner having
        a duct casing being hollow and having
            a cavity defined in the duct casing;
            an air inlet communicating with the cavity; and
            an air outlet communicating with the cavity;
        multiple UV generators mounted in the cavity in the duct casing and generating two types of UV when in operation, and one type of the UV having a wavelength in an extent from 160 to 300 nanometer (nm), and the other type of the UV having a wavelength in an extent from 220 to 300 nm; and
        an air pump connected to the air outlet and generating an outward air suction force through the air outlet, and
    a water cleaner connected to the UV cleaner and having
        a duct casing connected to the duct casing of the UV cleaner and having
            a cavity defined in the duct casing of the water cleaner;
            an air inlet communicating with the cavity in the duct casing of the water cleaner; and
            an air outlet communicating with the cavity in the duct casing of the water cleaner;
        multiple sprinkling tubes mounted in the cavity in the dust casing of the water cleaner and each sprinkling tube having multiple nozzles defined in the sprinkling tube;
        an inlet hose mounted in the duct casing of the water cleaner and communicating with the cavity of the duct casing; and
        an outlet hose mounted in the duct casing of the water cleaner and communicating with the cavity of the duct casing.

2. The air purifier as claimed in claim 1, wherein the nozzles in each sprinkling tube face the air inlet in the duct casing of the water cleaner.

3. The air purifier as claimed in claim 2, wherein the water cleaner further has an overflow hose mounted in the duct casing of the water cleaner above the outlet hose and communicating with the cavity of the duct casing.

* * * * *